United States Patent

Mochizuki et al.

Patent Number: 5,825,532
Date of Patent: *Oct. 20, 1998

[54] MICROSCOPIC SYSTEM INTEGRATED WITH WIDE-SCREEN TELEVISION

[75] Inventors: Ryo Mochizuki; Shinrokuro Nagashima; Hiroshi Saito, all of Tokyo, Japan

[73] Assignee: NHK Engineering Services, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 614,851

[22] Filed: Mar. 12, 1996

Related U.S. Application Data

[63] Continuation of Ser. No. 317,806, Oct. 4, 1994, abandoned.

[30] Foreign Application Priority Data

Oct. 4, 1993 [JP] Japan ................................. 5-247740

[51] Int. Cl.$^6$ .............................. G02B 21/00; A61B 1/04
[52] U.S. Cl. ......................... 359/368; 359/363; 359/376; 348/75; 348/79
[58] Field of Search .................................. 359/362–363, 359/368–370, 376, 378, 462–465, 467–470, 618; 348/42, 49, 51, 54, 64, 80

[56] References Cited

U.S. PATENT DOCUMENTS

| | | | |
|---|---|---|---|
| 4,072,967 | 2/1978 | Dudley | 359/465 |
| 4,143,938 | 3/1979 | Feinbloom | 359/363 |
| 4,395,731 | 7/1983 | Schoolman | 348/53 |
| 4,588,259 | 5/1986 | Sheiman | 359/465 |
| 4,598,311 | 7/1986 | Belliua | 348/79 |
| 4,641,328 | 2/1987 | Fujise | 378/8 |
| 4,740,836 | 4/1988 | Craig | 348/49 |
| 4,768,099 | 8/1988 | Mukai | 358/448 |
| 4,791,478 | 12/1988 | Tredwell et al. | 348/42 |
| 5,006,872 | 4/1991 | Parker | 359/363 |
| 5,181,102 | 1/1993 | Artigalas | 358/56 |
| 5,374,956 | 12/1994 | Kanno | 348/71 |
| 5,396,347 | 3/1995 | Kaneko | 358/448 |
| 5,583,566 | 12/1996 | Kanno et al. | 348/75 |

FOREIGN PATENT DOCUMENTS

| | | | |
|---|---|---|---|
| 2157843 | 12/1973 | Germany . | |
| 4104836 | 1/1992 | Germany . | |
| 63-240851 | 6/1988 | Japan . | |
| 324410 | 11/1992 | Japan | 359/376 |
| 8804786 | 6/1988 | WIPO . | |

OTHER PUBLICATIONS

English Abstract of Japanense Reference No. 1–319721, Dec 26, 1989.
English Abstract of Japanense Reference No. 4–324410, Nov. 13, 1992.
Enlish Abstract of Japanese Reference No. 57–208772, Published on Dec. 21, 1982.
English Abstract of Japanese Reference No. 59–300390, Published on Feb. 17, 1989.

*Primary Examiner*—Thong Nguyen
*Attorney, Agent, or Firm*—Hoffman, Wasson & Gitler

[57] ABSTRACT

Disclosed hereby is a microscopic system integrated with wide-screen television in which a medical information is combined with an image signal picked up by an imaging device including a microscope, a wide-screen television camera and an adaptor for mounting the camera on the microscope; the synthesized image signal is transmitted to be recorded/reproduced and the synthesized image is displayed as a stereoscopic image.

3 Claims, 3 Drawing Sheets

MICROSCOPIC SYSTEM INTEGRATED WITH WIDE-SCREEN TELEVISION

This application is a continuation of application Ser. No. 08/317,806 filed on Oct. 4, 1994, now abandoned.

BACKGROUND OF THE INVENTION

The present invention relates to a microscopic system integrated with wide-screen television in which a camera for television having a horizontally widened screen (hereinafter referred to as "wide-screen television") having for example a height to width ratio of 9:16 is mounted on a microscope so as to display an image from the microscope as a stereoscopic image.

In a conventional case where only a microscope is used in an operation such as of neurosurgery, there has been a limitation that only a main operator who is in charge of the medical operation and an assistant to him/her are able to see an image of the region to be operated. In recent years, however, a television picture is used to provide an image thereof, for example, to anesthetist, nurse and intern who are involved in the operation. This helps smoothing of a cooperated work.

Further, as a method for obtaining a stereoscopic image, television cameras are set on the optical paths, respectively, of the side scopes for the assistant which are provided on the left and right of the microscope. The outputs from the cameras are recorded in two VTRs, respectively, and are reproduced by using a system in which they are delivered to a display while the two VTRs are synchronously operated.

In the above conventional example, however, since the conventional television system is used, its practicalness is limited, for example, due to an insufficient image information resulting from a low resolution or due to degradation in color reproducibility of the image recorded in the VTRs.

Further, methods for displaying such image includes: a method in which two monitors or screens and polarizing plate/glasses are used; and a method in which the left and right images are alternately reproduced on one monitor or screen and are taken into left and right eyes by liquid crystal shutter glasses to obtain a stereoscopic image. Thus, there have been the following problems:

1) A long time period (5 to 6 hours) of watching is not endurable because of tired eyes due to the fact that the amount of light entering the eyes is reduced by filter or shutter or due to the fact that flickering is sensed.
2) It is difficult to obtain identical characteristics for the left and right imaging lenses/cameras and uniformity in such as hue and luminosity of the left and right monitors for providing a stereoscopic vision.
3) Only an expert can handle such as a synchronous operation of the two VTRs.

SUMMARY OF THE INVENTION

The present invention has been made to solve the above problems. It is an object of the present invention to provide a microscopic system integrated with wide-screen television in which an image from the microscope picked up by one wide-screen television camera is transmitted as an image signal of one system and is displayed as a stereoscopic image.

To achieve the above object, a microscopic system integrated with wide-screen television according to the present invention comprises the following construction.

Accordingly, there is provided a microscopic system integrated with wide-screen television having a wide-screen television camera mounted on a microscope to display an image from the microscope as a stereoscopic image, comprising: imaging means having the microscope, the wide-screen television camera and an adaptor for mounting the camera on the microscope; synthesizing means for combining a medical information with an image signal picked up by the imaging means; recording/reproduction means for recording/reproducing the image signal synthesized at said synthesizing means; and display means for displaying the synthesized image as a stereoscopic image.

In the above construction, an image signal picked up by the imaging means having a microscope, a wide-screen television camera and an adaptor for mounting the camera on the microscope is combined with a medical information, and the synthesized image signal is transmitted to be recorded/reproduced and the synthesized image signal is displayed as a stereoscopic image.

Other objects of the present invention will be apparent from the accompanying drawings and the following detailed description.

DESCRIPTION OF THE PREFERRED EMBODIMENT

A preferred embodiment of the present invention will now be described in detail with reference to the drawings.

Figure 1:
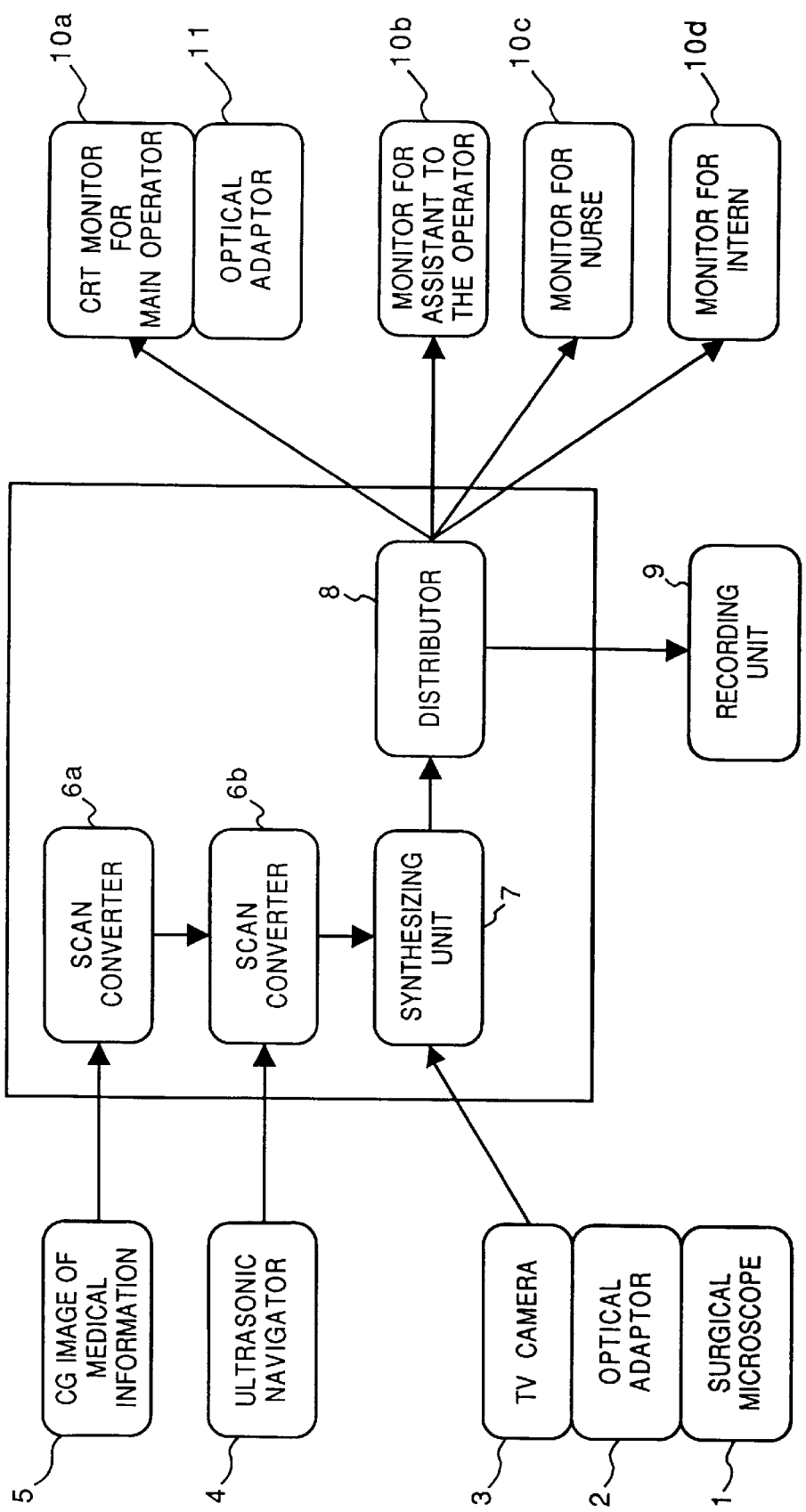
FIG. 1 is a block diagram showing the construction of a microscopic system integrated with wide-screen television according to an embodiment.

FIG. 1 illustrates the overall construction of a. microscopic system integrated with wide-screen television according to the present embodiment. Referring to FIG. 1, surgical microscope 1 is a binocular microscope which is used in an operation for example of neurosurgery where fine and accurate treatment is required. An imaging system optical adaptor 2 outputs the images for the left and right eyes, respectively, from the binocular microscope 1. A wide-screen television camera 3 is a high-vision (HDTV) camera, for example, having a vertical to horizontal ratio, V:H, of 9:16 (hereinafter referred to as "television camera"). The images for left and right eyes from the connected imaging system optical adaptor 2 are picked up as one image signal obtained by joining the two images each having a V:H=9:8.

Scan converters 6a, 6b are provided to convert a medical information 5 in the form of an analyzed CG image of X-ray CRT, MRI, MRA, SAS (Surface Anatomy Scan), DSA (Digital Subtraction Angeography), etc., and such as an ultrasonic induced image from the ultrasonic navigator 4 so that they may be combined with the image signal from the television camera 3. A synthesizing unit 7 provides an synthesized output by combining the image signal from the television camera 3 and the image signal from the scan converters 6a, 6b. A distributor 8 distributes the image signal synthesized at the synthesizing unit 7 to a recording/reproduction system and to a display system of a wide-screen television system which will be described later. A recording unit (such as VTR) 9 serves as the recording/reproduction system.

What is denoted by numeral 10a is a CRT monitor (monitor) for the main operator of an operation. By displaying in accordance with the delivered signal, left and right images having a parallax corresponding to the left and right are respectively formed on screen areas which are obtained by dividing the horizontally widened display screen (V:H= 9:16) substantially into two parts on the left and right. An optical adaptor 11 serves as an auxiliary unit for watching, which permits a stereoscopic vision by causing the respective images of the left and right portions on the screen of the monitor 10a to be diffracted so that they are substantially parallel to the left and right eyes of the watcher. Numerals 10b to 10d denote monitors, respectively, on which assistant to the operation, nurse and intern can see the image as it is or the same image as that of the main operator by using the optical adaptor 11.

In the above construction, the images for the left and right eyes from the binocular microscope 1 are picked up by the wide-screen television camera 3 using the imaging system optical adaptor 2 in a manner joining them into the left and right sides of one screen. The left and right images are displayed next to each other as an image signal of one system on the display screens of the monitors 10a~10d of the wide-screen television system. A stereoscopic vision becomes possible through the optical adaptor 11 serving as the auxiliary unit for watching which allocates the left side screen and the right side screen to the left and the right eyes, respectively.

A description will now be given in further detail of construction and function of the above described imaging system optical adaptor 2 and optical adaptor 11. The imaging system optical adaptor 2 will first be described.

Figure 2:
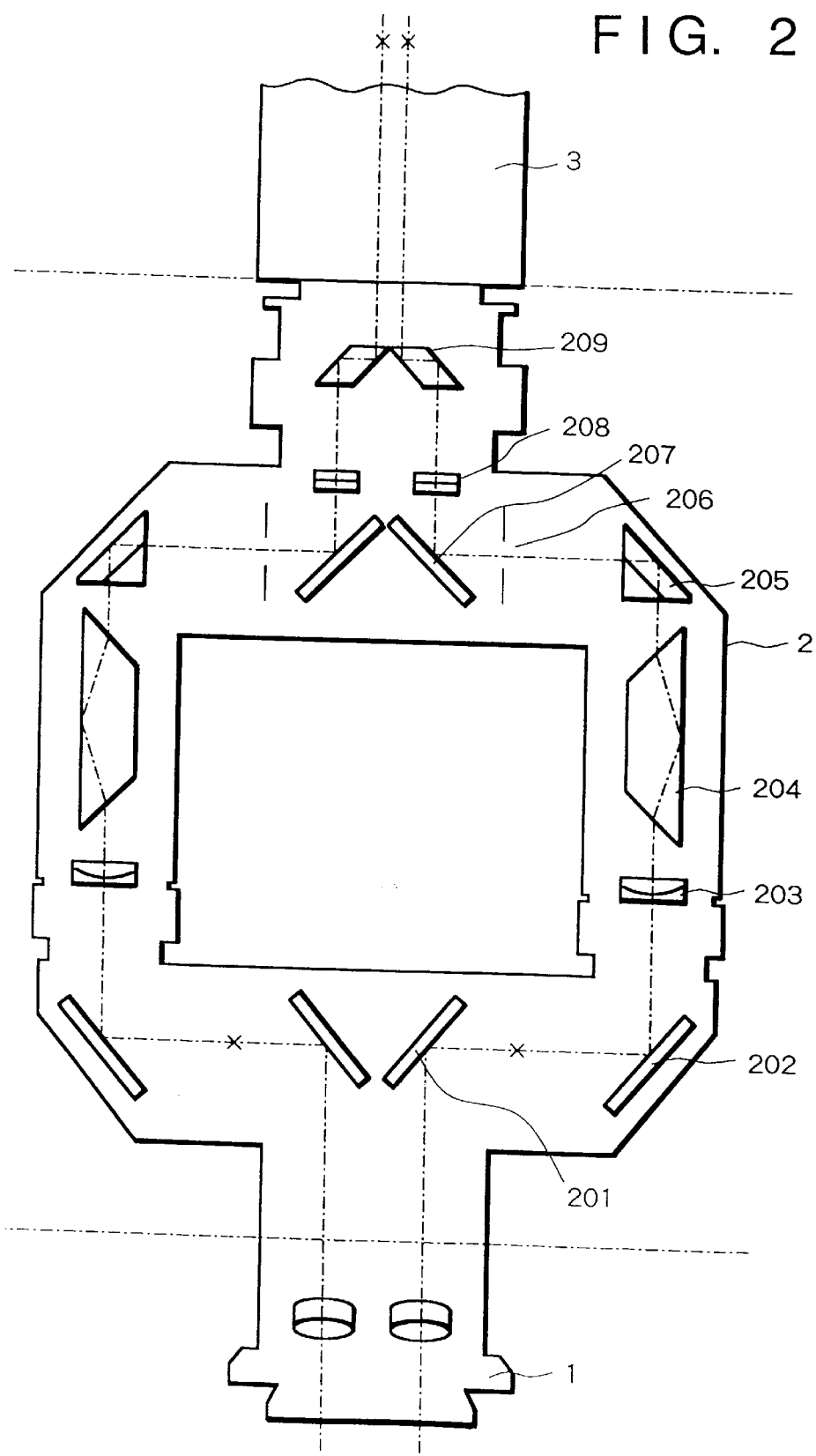
FIG. 2 illustrates the construction of optical adaptor 2 as shown in FIG. 1.

FIG. 2 illustrates the construction of the imaging system optical adaptor 2 for connecting the one television camera 3 such as a high-vision (HDTV) camera to the surgical binocular microscope 1.

As shown in FIG. 2, disposed respectively symmetrically in the imaging system optical adaptor 2 are mirrors 201, 202, 207, lenses 203, 208, prisms 205, 209, irises 206 and rotating units (image rotator) 204 for correcting the image in the viewing area to a rectified image. It is provided to bring images of the operation region from the surgical binocular microscope 1 into the imaging range of the television camera 3 by inputting them through the taking opening of the binocular microscope as shown by the broken line.

With the above described optical adaptor 2, the left and right images of the region to be operated identical to those conventionally seen by the main operator through the surgical binocular microscope 1 may be joined together on a screen having an aspect ratio (9 to 16) of the wide-screen television. It may be set such that the centers of the respective images on the left and the right (in the case of naked-eyes parallel viewing method) or on the right and the left (in the case of naked-eyes crossed viewing method) are brought to the screen centers of the left and right sides of the screen.

It should be noted that the optical adaptor 2 may be applied not only to a surgical binocular microscope but also to an endoscope, etc., which requires a stereoscopic vision.

By projecting the image formed as described onto a monitor, it is possible to obtain a stereoscopic vision. Methods for such stereoscopic vision include a method by naked eyes without using an auxiliary device and a method relying on an auxiliary device for watching.

The stereoscopic vision based on naked-eye viewing includes a parallel method and a crossing method. In the parallel method, the image for the left eye is disposed on the left side and the image for the right eye is disposed on the right side. On the contrary, in the crossing method, the image for the left eye is disposed on the right side and the image for the right eye is disposed on the left side. Methods for achieving this include: a mechanical method performed by rotating the image rotator 204 of the imaging system optical adaptor 2 and the camera 3; and an electronic method which uses a frame memory, an image synthesizing unit, etc.

Figure 3:
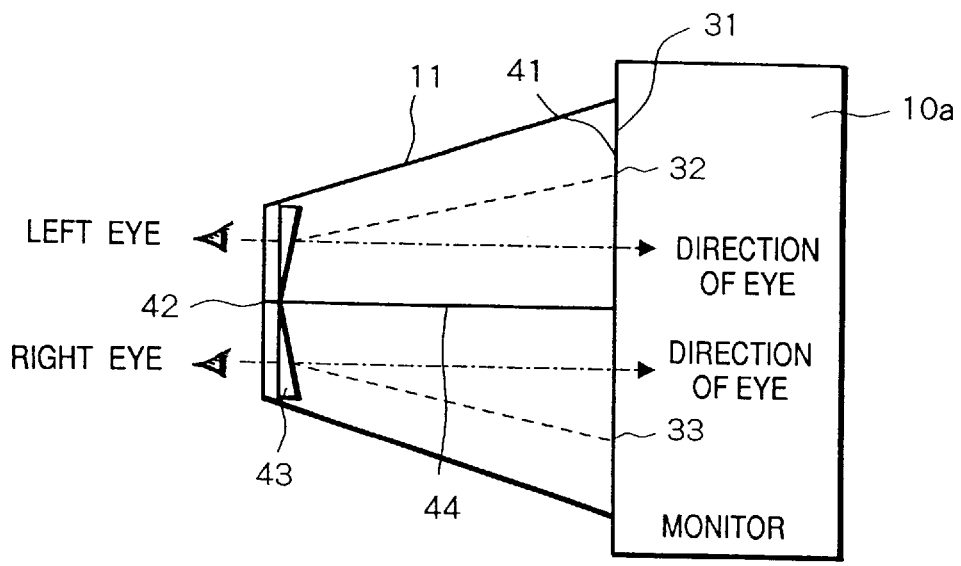
FIG. 3 is a top view showing connection between monitor 10a and optical adaptor 11.
Figure 4:
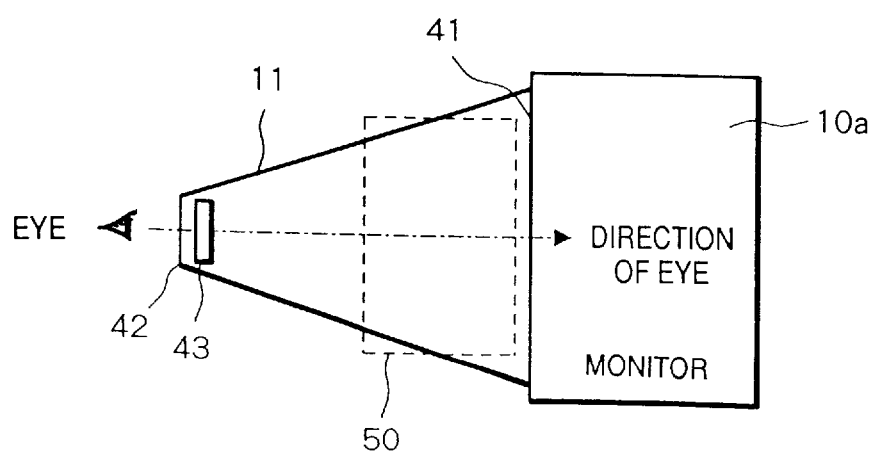
FIG. 4 is a side view showing connection between the monitor 10a and the optical adaptor 11.

A description will now be given with respect to the optical adaptor 11 which serves as an auxiliary unit for watching. FIG. 3 is a top view of the monitor 10a to which the optical adaptor 11 is added and FIG. 4 is a side view thereof. As shown in FIG. 3, the optical adaptor 11 has an aperture 41 having an area corresponding to the display screen 31 of the monitor 10a and an eyepiece portion 42 formed in the shape of a tube extended from the aperture 41 and containing wedge-like prism and lens 43 which will be described later. A partition 44 for dividing the tube into the left and right is provided at the internal space thereof.

It should be noted that, the above wedge-like prism and lens 43 is provided so that, when two lines (typical viewing axes) 32, 33 respectively connecting the left and right eyes of the watcher and the center points of the left portion and the right portion of the screen of the monitor 10a are incident upon the left and right eyes of the watcher, a displayed image on the screen which, in effect, serves as the gazing point may be gazed within a predetermined range of distance.

Further, the tubular optical adaptor 11 corresponds to the size of the display screen 31 of the monitor 10a. The dimensions between the eyepiece 42 and the aperture 41 are varied while maintaining the similarity thereof so that the eyepiece 42 having the same optical characteristic may be adapted to various screen dimensions of the monitor 10a. In other words, even when the monitor is relatively small as a broken line portion 50 shown in FIG. 4, it may be adapted by cutting the screen side of the optical adaptor 11 to provide an aperture, so that viewing angle of the watcher is not changed even with changes in the dimensions of a screen.

In this manner, according to this embodiment, the screen characteristic (V:H=9:16) of wide-screen television is utilized so that the left and right microscopic images from the binocular microscope are picked up by one wide-screen television camera in a manner disposed next to each other (9:8×2) on the left and right sides of one screen. The picked up image on which medical information is combined or superimposed is displayed on a monitor of the wide-screen television. A stereoscopic image may be obtained from it as it is or by means of an optical adaptor attached to the monitor. Further, the stereoscopic image may be recorded/reproduced by a single VTR.

Thus, the following advantages may be obtained according to the system of this embodiment:

1) Since an operation is proceeded while watching an electronic image, a medical information necessary for the operation is accessible on an image of the operation as required by opening a multimedia window, whereby an efficient operation may be performed. Further, during the operation, an ultrasonic image or endoscope may be displayed within the microscopic image either macroscopically (showing state of the ultrasonic terminal or the location of the terminal end of the endoscope) or microscopically (showing ultrasonic image or endoscopic image), whereby the operator can control the current condition in a multi-dimensional way.

2) Since the optical axis of the microscope and the viewing axis of the surgical operator may be separated from each other, the operator can render the operation while maintaining one's best posture without restriction in the posture due to the position of the patient.

3) In order to properly support the operator, it is very important for the staff of the operation (assistant to the operation, nurse, anesthetist, etc.) to sufficiently understand the detail of the surgical operation which is currently being performed. In the present system, the operation staff is able to stereoscopically view a monitor image at the same high resolution as that viewed by the operator. There is another advantage that, if the operator refers to necessary medical images during the operation, such images, too, may be shared by the operation staff so that the detail of the operation is well understood.

4) A support for the operator during the operation may be provided by means of a guidance/advice by a noted specialist who is remote from the operation.

5) Records in high resolution image of the operation may be collected to construct a database to maintain it as a library so that it may be used in transmission or education of the operating procedure by a noted specialist with respect to a typical case.

6) When the present system is extensively established, the operator is able to continuously comprehend the region of surgical operation by means of a navigation system. While monitoring the state within the brain during the operation by means of an ultrasonic image to compare it with an image data before the operation, the operator can proceed the operation with maintaining an interactive exchange with a person who guides the operator through the operation.

As has been described, according to this embodiment, an image from a microscope picked up by a single wide-screen television camera may be displayed as a stereoscopic image.

While the present invention has been described by way of a preferred embodiment thereof, the present invention is not limited by the above embodiment and various modifications thereof are possible within the scope defined by the claims.

What is claimed is:

1. A high-definition television (HDTV) stereoscopic microscope system for performing an operation while watching an HDTV monitor, comprising:

an optical adaptor to:
input left and right images from a binocular microscope, respectively,
route said the inputted left and right images so that they can be viewed by the left and right eyes of a human being, and
output the left and right images to an HDTV camera;
conversion means for converting medical information relating to a patient into images according to the region to be operated so as to be superimposed on the left and right images from said HDTV camera;
superimposing means for superimposing the converted medical information on the left and right images; and
display means for displaying the left and right images superimposed medical information as a stereoscopic live image on said HDTV monitor.

2. The system according to claim 1, further comprising recording/reproducing means for recording/reproducing signals of the superimposed stereoscopic image.

3. The system according to claim 2, further comprising a distributor for distributing the signals of the superimposed stereoscopic image to one or more high-definition television (HDTV) monitor and said recording/ reproducing means.

* * * * *

UNITED STATES PATENT AND TRADEMARK OFFICE
CERTIFICATE OF CORRECTION

PATENT NO. : 5,825,532
DATED : October 20, 1998
INVENTOR(S) : Ryo Mochizuki et al.

It is certified that error appears in the above-identified patent and that said Letters Patent is hereby corrected as shown below:

On the cover page, under the section "References Cited" and "Other Publications", after English Abstract of Japanese Reference, change "No. 59-300390" to --59-030390--.

Signed and Sealed this

Sixteenth Day of March, 1999

*Attest:*

Q. TODD DICKINSON

*Attesting Officer*     *Acting Commissioner of Patents and Trademarks*